US00PP12589P2

(12) United States Plant Patent
Zapfel

(10) Patent No.: US PP12,589 P2
(45) Date of Patent: Apr. 30, 2002

(54) BIDENS PLANT NAMED 'GOLDEN STAR'

(75) Inventor: Hermann Zapfel, Angelbachtal (DE)

(73) Assignee: Gebr. Leinert, Angelbachtal (DE)

( * ) Notice: Subject to any disclaimer, the term of this patent is extended or adjusted under 35 U.S.C. 154(b) by 0 days.

(21) Appl. No.: 09/484,658

(22) Filed: Jan. 18, 2000

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database 2001/01 Feb. 6, 2001, GTI Jouve Retrieval Software, Citation for 'Golden Star'.*

* cited by examiner

*Primary Examiner*—Bruce R. Campell
*Assistant Examiner*—Annette H. Para
(74) *Attorney, Agent, or Firm*—C. A. Whealy

(57) ABSTRACT

A distinct cultivar of Bidens plant named 'Golden Star', characterized by its compact, mostly upright and somewhat outwardly spreading plant habit; freely branching, dense and bushy appearance; early and continuous flowering; large bright yellow inflorescences; and good garden performance.

1 Drawing Sheet

BACKGROUND OF THE INVENTION

The present invention relates to a new and distinct cultivar of Bidens plant, botanically known as *Bidens ferulifolia* (*Jacq.*) *DC* and referred to by the cultivar name Golden Star.

The new Bidens is a naturally-occurring whole plant mutation of an unnamed selection of *Bidens ferulifolia* (*Jacq.*) *DC*. The new Bidens was discovered by the Inventor in a controlled environment in Angelbachtal, Germany, within a population of the unnamed selection. The selection of this plant was based on its large bright yellow inflorescences and compact plant habit.

Asexual propagation of the new cultivar by terminal cuttings at Angelbachtal, Germany, has shown that the unique features of this new Bidens are stable and reproduced true to type in successive generations.

SUMMARY OF THE INVENTION

The following traits have been repeatedly observed and are determined to be the unique characteristics of 'Golden Star'. These characteristics in combination distinguish 'Golden Star' as a new and distinct cultivar:

1. Compact, mostly upright and somewhat outwardly spreading plant habit.
2. Freely branching, dense and bushy appearance.
3. Early and continuous flowering.
4. Large bright yellow inflorescences held above the foliage on strong wiry peduncles.
5. Good garden performance.

The cultivar Golden Star has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new Bidens, showing the colors as true as it is reasonably possible to obtain in colored reproductions of this type. Colors in the photographs may differ slightly from the color values cited in the detailed botanical description which more accurately describe the actual colors of the new Bidens.

The photograph at the top of the sheet comprises a top perspective view of a typical flowering plant of 'Golden Star'.

The photograph at the bottom of the sheet is a close-up view of a typical plant of 'Golden Star'.

DETAILED BOTANICAL DESCRIPTION

The following observations, measurements and values describe plants of the new cultivar grown in 15-cm container in Snohomish, Wash., under outdoor nursery conditions which approximate commercial production. Plants used for the description and photographs were about four months old.

Color references are made to The Royal Horticultural Society Colour Chart except where general terms of ordinary dictionary significance are used.

Botanical classification: *Bidens ferulifolia* (*Jacq.*) *DC* cultivar Golden Star.

Parentage: Naturally-occurring whole plant mutation of unnamed selection of *Bidens ferulifolia* (*Jacq.*) *DC*, not patented.

Propagation:

*Type.*—By terminal cuttings.

*Time to develop roots.*—About 2 to 3 weeks at 22° C.

*Root description.*—Fibrous and freely branching.

Plant description:

*Appearance.*—Herbaceous container and garden plant. Compact; mostly upright and outwardly spreading growth habit. Full plants with dense foliage with inflorescences held above the foliage on strong wiry peduncles.

*Crop time.*—From planting rooted cuttings, about 8 to 12 weeks are required to produce a finished, flowering plant in a 15-cm container.

*Vigor.*—Moderately vigorous.

*Plant height.*—About 25 cm.

*Plant spread.*—About 35 cm.

*Stem diameter.*—About 1 mm.

*Stem color.*—Upper stems: 144A. Lower stems: 166A.

*Foliage description.*—Leaves opposite, single. Length: About 2.5 cm. Width: About 1.4 cm. Shape: Dissected; pinnatifid. Apex: Acute. Base: Attenuate. Aspect: Mostly flat. Texture: Smooth. Petiole length: About 1 cm. Petiole diameter: About 1 mm. Color: Young foliage, upper surface: Close to 144A. Young foliage, lower surface: Close to 144B. Fully expanded foliage, upper surface: Close to 146A. Fully expanded foliage, lower surface: Close to 146B.

Inflorescence description:

*Appearance.*—Daisy-type composite inflorescence form; actinomorphic. Disc and ray florets arranged acropetally on a capitulum. Inflorescences displayed above and beyond the foliage on strong wiry peduncles; peduncles arising from upper leaf axils. Continuously flowering, numerous inflorescences open at the same time. Inflorescences last about one to two weeks. Inflorescences persistent.

*Flowering response.*—Plants flower continuously from April to October in the Northern Hemisphere.

*Fragrance.*—Not detected.

*Inflorescence size.*—Diameter: About 2 cm. Depth (height): About 5 mm. Diameter of disc: About 3 mm.

*Inflorescence buds.*—Length: About 4 mm. Diameter: About 2.5 mm. Shape: Oblong. Color: 146A.

*Ray florets.*—Length: About 9 mm. Width: About 7 mm. Shape: Oblong. Apex: Rounded to retuse. Base: Attenuate. Margin: Entire. Aspect: Mostly flat. Texture: Smooth, satiny. Number of ray florets per inflorescence: About five in a single whorl. Color: When opening, upper and lower surfaces: 9A to 12A to 14A. Fully opened, upper and lower surfaces: 14A to 12A to 14B; fading to 9A.

*Disc florets.*—Shape: Tubular; fluted at apex. Number of disc florets per inflorescence: About 12. Length: About 4 mm. Width, at apex and base: About 1 mm. Color: Immature: Light green, 154A. Mature: Apex: 15A to 17A. Base: Light green, 154A, to white, 155D.

*Phyllaries.*—About Quantity: About 6 to 8 per inflorescence. Length: About 4 mm. Width: About 2 mm. Shape: Elliptic. Color, both surfaces: 146A.

*Peduncle.*—Length: About 1.75 cm. Diameter: Less than 1 mm. Aspect: Very flexible, wiry; strong; inflorescences held above and beyond foliage; angled about 30 to 45° to the stem. Texture: Smooth. Color: 144A.

*Reproductive organs.*—Androecium: Present on disc florets only. Anther color: 15A to 17A, Pollen amount: Moderate. Pollen color: 17A. Gynoecium: Present on ray and disc florets. Seed: Seed development has not been observed.

Disease resistance: Resistance to pathogens common to Bidens has not been observed on plants of the new Bidens.

Garden performance: Plants of the new Bidens have exhibited good garden performance.

It is claimed:

1. A new and distinct cultivar of Bidens plant named 'Golden Star', as illustrated and described.

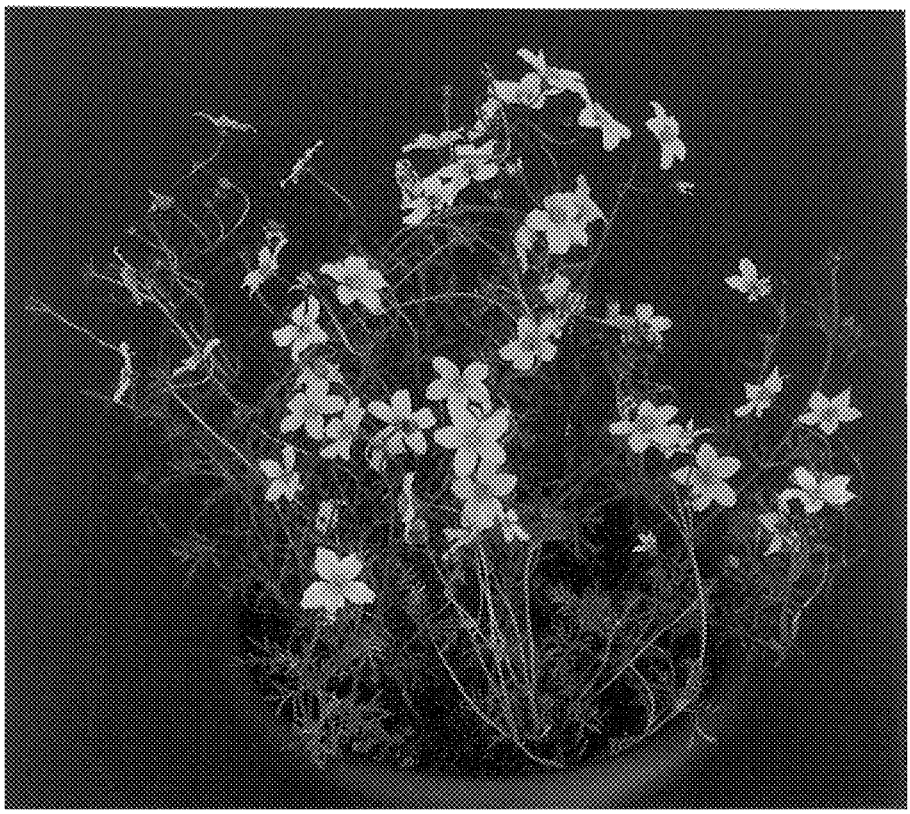
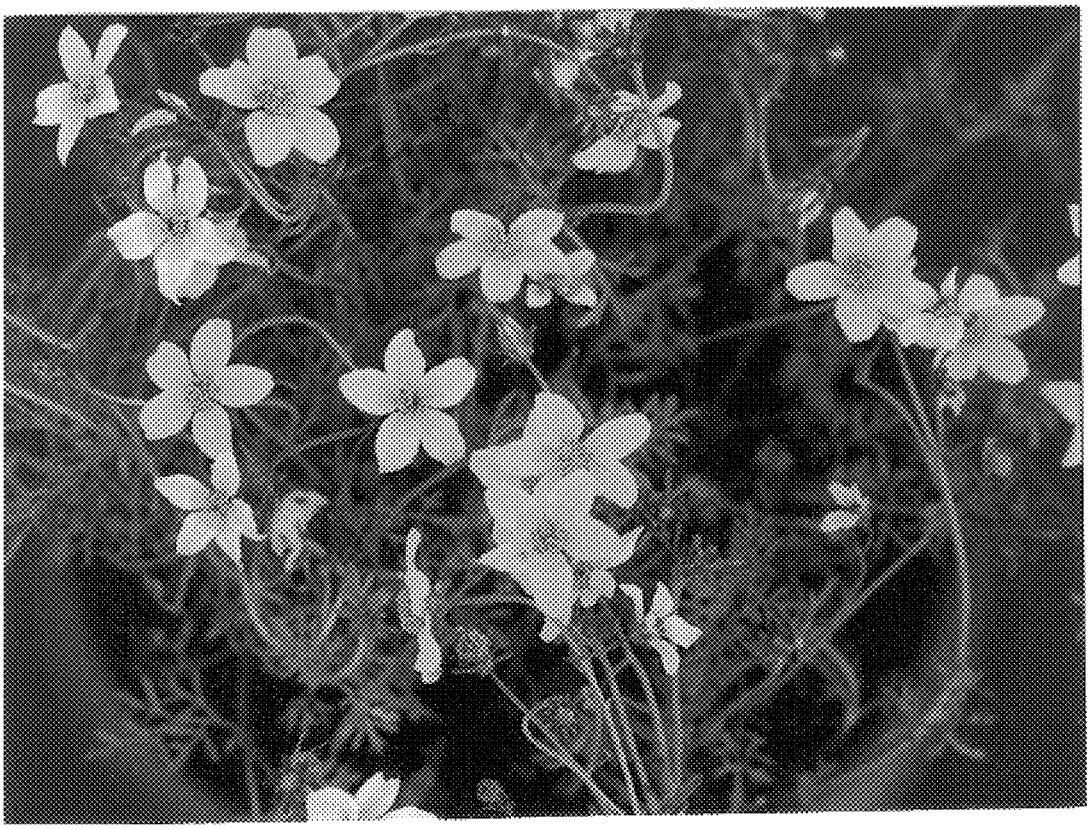

* * * * *